United States Patent [19] [11] 4,045,206
Convent [45] Aug. 30, 1977

[54] SYNERGISTIC HERBICIDAL COMPOSITION COMPRISING N-(BUTOXYMETHYL)-6'-TERT-BUTYL-2-CHLORO-o-ACETOTOLUIDIDE AND METHABENZTHIAZURON

[75] Inventor: Bernard Convent, Leernes, Belgium

[73] Assignee: Monsanto Company, St. Souis, Mo.

[21] Appl. No.: 605,569

[22] Filed: Aug. 18, 1975

[51] Int. Cl.$^2$ .......................... A01N 9/12; A01N 9/20; A01N 9/02
[52] U.S. Cl. .......................................... 71/90; 71/76; 71/118
[58] Field of Search .................................. 71/90, 118

[56] References Cited

U.S. PATENT DOCUMENTS

| | | | |
|---|---|---|---|
| 2,756,135 | 7/1956 | Searle | 71/90 |
| 3,442,945 | 5/1969 | Olin | 71/118 |
| 3,547,620 | 12/1970 | Olin | 71/118 |

OTHER PUBLICATIONS

Pfeiffer, "Synergistic urea-triazine herbicide", (1972), CA 77, No. 71432t. (1972).
Fischer, "Herbicidal benzothiodiazinone urea etc.", (1972) CA 78, No. 93634h. (1973).
Hack et al., "Herbicide Composition", (1974) CA 81, No. 34557z (1974).

*Primary Examiner*—Glennon H. Hollrah
*Attorney, Agent, or Firm*—William I. Andress; Donald W. Peterson

[57] ABSTRACT

A synergistic herbicidal composition comprising as the active ingredient a mixture of N-(butoxymethyl)-6'-tert-butyl-2-chloro-o-acetotoluidide and N-(2-benzthiazolyl)-N,N'-dimethylurea and use of said composition particularly in cereal crops.

8 Claims, No Drawings

SYNERGISTIC HERBICIDAL COMPOSITION COMPRISING N-(BUTOXYMETHYL)-6'-TERT-BUTYL-2-CHLORO-o-ACETOTOLUIDIDE AND METHABENZTHIAZURON

BACKGROUND OF THE INVENTION

1. Field of the Invention

The invention herein pertains to the field of herbicides. In particular, the invention pertains to a synergistic herbicidal composition having as the active ingredient a mixture of N-(butoxymethyl)-6'-tert-butyl-2-chloro-o-acetotoluidide and N-(2-benzthiazolyl)-N,N'-dimethylurea (common name methabenzthiazuron). The herbicidal composition herein has particular application in the control of undesired plants associated with cereal crops, e.g., wheat and barley.

2. Description of the Prior Art

It is known in the prior art to use various substituted ureas as herbicides, either individually or in combination with various other herbicidal compounds. In such urea compounds, the N and N' atoms may be substituted with heterocyclic, aryl or aliphatic substituents, e.g., benzthiazolyl, phenyl, or substituted phenyl, phenoxy or substituted phenoxy groups, alkyl, alkenyl, alkoxy groups, but other groups may also be used.

A wide variety of chemical compounds have been admixed with various members of the above-mentioned substituted ureas in efforts to discover new herbicidal compositions having unique additive, antagonistic or synergistic properties with respect to different weed plants associated with various crop plants. Illustrative of prior art herbicide mixtures containing substituted ureas and other compounds are those containing a trichlorophenylacetic acid, its salts, amides or esters (U.S. Pat. No. 3,163,516); alkyl- and/or halo-substituted phenoxyacetic acid, -salt, -amide or -ester (U.S. Pat. No. 2,709,648); trichlorobenzoic acid or its salts (U.S. Pat. No. 3,253,903); halo- and nitro-substituted diphenyl ethers (U.S. Pat. No. 3,484,230); triazines (U.S. Pat. No. 3,022,150); CF$_3$/NO$_2$-substituted toluidine (U.S. Pat. No. 3,373,010) and thiolcarbamic acid esters (U.S. Pat. No. 3,095,299). U.S. Pat. No. 2,655,445 and British Pat. Nos. 1,253,143; 1,255,258 and 1,260,460 disclose a generic class of herbicidal trisubstituted ureas which may be used alone or in conjunction with other named herbicidal compounds.

The particular substituted urea of interest and use herein as a component of the combination herbicide of the present invention, i.e., N-(2-benzthiazolyl)-N,N'-dimethylurea ("methabenzthiazuron" for brevity), is a known compound having herbicidal properties. The preparation of methabenzthiazuron and its use as a herbicide is disclosed in U.S. Pat. No. 2,756,135. Herbicidal compositions of methabenzthiazuron are available as Tribunil 70WP.

A variety of chemical compounds have been admixed with methabenzthiazuron in efforts to discover new herbicidal compositions having unique herbicidal properties with respect to different plants. Illustrative of prior art herbicide mixtures containing methabenzthiazuron and other herbicidal compounds are those containing 2-(chloro and methyl)-4-chlorophenoxyacetic and propionic acid salts and esters (U.S. Pat. 3'3,682,614); or 1-(3-chloro-4-methylphenyl)-3,3-dimethylurea (British Pat. No. 1,374,217); or 2-chloro-4,6-bis(ethylamino)-s-triazine (Belgian Pat. No. 772238); or 3-cyclohexyl-5,6-trimethylene-uracil (French Pat. No. 1,597,542); or N-1,1-dimethylpropynyl-3,5-dichlorobenzamide (British Pat. No. 1,330,177); or an ester of a halogenated alkanoic acid and a halogenated alkanol or benzyl alcohol; this mixture may optionally contain 2,6-dichlorobenzonitrile (Belgian Pat. No. 813,833).

It is also known in the prior art to use various 2-halo-2'6'-dialkyl-N-(alkoxyalkyl) acetanilides as herbicides either individually or in combination with other herbicidal compounds. For example, U.S. Pat. No. 3,551,132 discloses the herbicidal use of 2-chloro-2',6'-diethyl-N-(methoxymethyl) acetanilide (common name alachlor) admixed with 3'-(carbamoyloxy) anilides. British Pat. No. 1,176,547 discloses the herbicidal use of a mixture of alachlor and linuron, i.e., 3-(3,4-dichlorophenyl)-1-methoxy-1-methylurea.

In still further particular, U.S. Pat. Nos. 3,442,945 and 3,547,620 both of which are also assigned to applicant's assignee, disclose a broad class of herbicidal 2-halo-2',6'-dialkyl-N-(alkoxyalkyl) acetanilides, expressly including N-(butoxymethyl)-6'-tert-butyl-2-chloro-o-acetotoluidide. This compound has tentatively been designated as "terbuchlor"; application is being made by applicant's assignee to the American Standards Institute for registration of this name as the common name for said compound. Hence, the term "terbuchlor" will sometimes be used hereafter in the specification for brevity. The 3,442,945 and 3,547,620 patents both disclose that the acetanilide compounds therein may be admixed with other herbicidal compounds, including certain trisubstituted ureas, such as linuron, monuron or diuron. However, methabenzthiazuron-type ureas are not disclosed in these patents.

To applicant's knowledge, there has been no recognition or disclosure in the prior art of a herbicidal composition comprising terbuchlor and a urea of the type including methabenzthiazuron, which together impart complementary, supplementary and/or synergistic action with respect, particularly, to undesirable vegetation associated with cereal crops, such as wheat and barley.

The phenomenon of synergism is well known to those skilled in the art and, in the herbicidal art, relates to herbicidal compositions of mixed components whose total herbicidal effect is unexpectedly greater than the additive effect of the individual components on particular plants or a spectrum of plants. The use of synergistic mixtures for the control of plant growth permits the utilization of a lesser total amount of herbicidal composition and/or lesser quantities of individual components in the compositon to obtain the same or improved results than are obtained when a greater amount of herbicidal composition containing only the individual components or additive mixtures thereof. The use of lesser quantities of active ingredients in a herbicidal composition may also increase the margin of crop safety in the use of those active ingredients.

The concepts of synergism and antagonism (i.e., negative, neutralizing or nullifying effect of one component on another component) in herbicidal combinations have been reduced to mathematical formulation and graphical representation by some authors. For example, by the method described by S. R. Colby in "Weeds", Vol. 15, No. 1 (1967) pages 20–22, the expected response of a combination of herbicides is obtained by taking the product of the percent-of-control values for the individual herbicides and dividing by $(100)^{n-1}$ where $n$ is the number of herbicides in the combination.

Another method of expressing synergism and antagonism is described by P. M. L. Trammes in "Netherlands Journal of Plant Pathology", 70 (1964), 73–80. By the Tammes method, a graphic representation is given of the effect of mixtures of herbicides. Each of the components is expressed as a coordinate on a graph and a quantitatively defined effect, e.g., a percent plant mortality, e.g., 50%, 85%, etc., is inserted in the graph. These values are obtained by interpolation. The line which connects the points is called an "isobole". With an isobole the effect of different proportions of the individual components can be evaluated. The Tammes isoboles method has proven reliable in evaluating the synergistic effect of the herbicidal composition of this invention.

As used herein the term "active ingredient" denotes a mixture of terbuchlor and methabenzthiazuron having the combined supplementary, complementary and synergistic properties unique to this mixture.

The term "plant" as used herein encompasses dormant seeds, germinant seeds, germinative seeds, emerging seedlings and established vegetation including roots and above-ground portions.

The term "control" as used herein is inclusive of the effects of killing, inhibiting the growth, reproduction or proliferation and removing, destroying or otherwise diminishing the occurrence or activity of plants and is applicable to any of the stated effects or combinations thereof.

SUMMARY OF THE INVENTION

The present invention relates to a synergistic herbicidal composition containing as the active ingredient therein a mixture of terbuchlor and methabenzthiazuron as above defined, and to the herbicidal use of such compositions particularly useful in cereal crops, e.g., wheat and barley, to control undesired plants such as *Lolium multiflorum, Polygonium lapathifolium, Sinapis arvenis, Stellaria media, Avena fatua, Alopecurus myosuroides* and *Matricaria chamomilla*.

DESCRIPTION OF PREFERRED EMBODIMENTS

Example

Terbuchlor may be prepared by methods generally known to the art. For example, in Example 4 of each of the above-cited U.S. Pat. Nos. 3,442,945 and 3,547,620, terbuchlor is prepared by reacting 2-tert-butyl-6-methyl-N-methyleneaniline and chloroacetyl chloride with n-butanol according to conditions noted in the example.

Methabenzthiazuron also may be prepared by known methods commonly used to prepare substituted ureas. For example, as disclosed in the above-mentioned U.S. Pat. No. 2,756,135 methabenzthiazuron can be prepared by the reaction of a 2-aminobenzothiazol with methyl isocyanate or with a suitably substituted carbamyl chloride.

Terbuchlor and methabenzthiazuron were tank mixed and applied to the surface of a sandy loam soil contained in plastic pots and previously sown with crop and weed seeds at 1 cm depth. Application of the mixed herbicide was made at a volume equivalent of 4000 4ha with a Devilibiss atomizer No. 152. Initial irrigation of 1 mm was applied by overhead means and subsequent watering requirements by subirrigation. The plants were visually observed approximately 3 weeks after sowing and the results recorded.

In the table below, the various plant species tested are identified according to the following abbreviations:

lol. mul. — *Lolium multiflorum*
Pol. lap. — *Polygonum Lapathifolium*
Sin arv. — *Sinapis arvensis*
Stel. med. — *Stellaria media*
Av. fat. — *Avena fatua*
Alop. myos. — *Alopecurus myosuroides*
Matric. cham. — *Matricaria chamomilla*

TABLE I

| Active Ingredient | Rate Kg/ha | Wheat | Barley | Lol. Mul. | Pol. lap. | Gal. ap. | Sin. arv. | Stel. med. | Av. fat. | Alop. myos. | Matric. cham. | |
|---|---|---|---|---|---|---|---|---|---|---|---|---|
| | 4 | 35 | 35 | 60 | 70 | 20 | 50 | 80 | 90 | 90 | 90 | (2) |
| | 2 | 35 | 20 | 100 | 25 | 15 | 50 | 70 | 80 | 85 | 65 | (2) |
| | 1 | 16 | 15 | 100 | 30 | 20 | 40 | 78 | 75 | 85 | 73 | (1) |
| Terbuchlor | | | | | | | | | | | | |
| | 0.5 | 5 | 5 | 85 | 13 | 5 | 33 | 43 | 53 | 68 | 70 | (1) |
| | 0.25 | 0 | 0 | 85 | 0 | 0 | 0 | 30 | 40 | 60 | 25 | (2) |
| | 0.125 | 0 | 0 | 50 | 0 | 0 | 0 | 20 | 30 | 20 | 15 | (2) |
| | 8 | 50 | 45 | 95 | 100 | 85 | 100 | 100 | 75 | 85 | 100 | (2) |
| | 4 | 0 | 15 | 45 | 100 | 85 | 100 | 100 | 85 | 90 | 100 | (2) |
| Methabenz-thiazuron | 2 | 0 | 0 | 33 | 73 | 8 | 98 | 95 | 20 | 60 | 100 | (1) |
| | 1.1 | 0 | 5 | 18 | 55 | 0 | 85 | 80 | 18 | 23 | 100 | (1) |
| | 0.5 | 0 | 0 | 20 | 15 | 0 | 20 | 30 | 10 | 10 | 100 | (1) |
| | 0.25 | 0 | 0 | 0 | 10 | 0 | 15 | 25 | 0 | 0 | 100 | (2) |

| Active Ingredient | Rate Kg/ha (3) | Wheat | Barley | Lol. Mul. | Pol. lap. | Gal. ap. | Sin. arv. | Stel. med. | Av. fat. | Alop. myos. | Matric cham. | |
|---|---|---|---|---|---|---|---|---|---|---|---|---|
| | 2 + 4 | 40 | 75 | 100 | 100 | 85 | 100 | 100 | 100 | 100 | 100 | (2) |
| | 2 + 2 | 25 | 55 | 100 | 100 | 60 | 100 | 100 | 100 | 100 | 100 | (2) |
| | 2 + 1 | 0 | 10 | 100 | 70 | 60 | 100 | 100 | 100 | 100 | 100 | (2) |
| | 1 + 4 | 20 | 75 | 100 | 100 | 80 | 100 | 100 | 100 | 100 | 100 | (2) |
| | 1 + 2 | 0 | 10 | 100 | 90 | 10 | 100 | 100 | 100 | 100 | 100 | (2) |
| | 1 + 1 | 0 | 5 | 100 | 100 | 10 | 100 | 100 | 80 | 100 | 100 | (2) |
| Terbuchlor | 0.5 + 4 | 35 | 65 | 100 | 100 | 55 | 100 | 100 | 100 | 100 | 100 | (2) |
| and | 0.5 + 2 | 0 | 45 | 100 | 85 | 20 | 100 | 100 | 80 | 100 | 100 | (2) |
| Methabenz- | 0.5 + 1 | 0 | 5 | 100 | 75 | 30 | 100 | 100 | 68 | 93 | 100 | (1) |
| thiazuron | 0.5 + 0.5 | 0 | 0 | 95 | 45 | 40 | 85 | 95 | 40 | 60 | 100 | (2) |
| | 0.5 + 0.25 | 0 | 0 | 99 | 30 | 50 | 85 | 80 | 60 | 50 | 100 | (2) |
| | 0.25 + 1 | 0 | 0 | 95 | 85 | 35 | 100 | 95 | 30 | 45 | 100 | (2) |
| | 0.25 + 0.5 | 0 | 0 | 85 | 50 | 20 | 90 | 90 | 40 | 45 | 99 | (2) |
| | 0.25 + 0.25 | 0 | 0 | 70 | 20 | 0 | 30 | 45 | 20 | 30 | 100 | (2) |
| | 0.125 + 1 | 0 | 0 | 70 | 40 | 10 | 85 | 80 | 20 | 20 | 100 | (2) |
| | 0.125 + 0.5 | 0 | 0 | 60 | 30 | 20 | 50 | 60 | 20 | 30 | 99 | (2) |

TABLE I-continued

| | | | Percent Control of Plants | | | | | | | | |
|---|---|---|---|---|---|---|---|---|---|---|---|
| 0.125 + 0.25 | 0 | 0 | 70 | 20 | 0 | 20 | 40 | 20 | 40 | 95 | (2) |

(1) Percent averages for four replications
(2) Percent averages for two replications
(3) Numbers in the first column refer to terbuchlor rates The synergistic response for terbuchlor/methabenzthiazuron herbicidal mixtures is well shown by data in Table I. Thus, consider the average rates of the three herbicides, i.e., terbuchlor, methabenzthiazuron and a mixture of the two, required to control 85% of the weeds ($GR_{85}$), and the average maximum rates of the herbicides for 15% or less growth reduction ($GR_{15}$) of the crop plants for illustrative purposes.

For example, in order to control Pol. lap. ($GR_{85}$), an undetermined amount greater than 4 kg/ha of terbuchlor alone is required; however, such rates are not selective for use with wheat and barley. Similarly, between 2 and 3 kg/ha of methabenzthiazuron are required for a $GR_{85}$, without injury to the crop plants. In contrast, terbuchlor/methabenzthiazuron mixtures of either 0.25 + 1.0, 1.0 + 1.0 or 1.0 + 2.0 kg/ha will selectively control Pol. lap. in wheat and barley with little or no injury to these crops. Also, a 0.5 + 2.0 kg/ha mixture will selectively control Pol. lap. in wheat. The 1.0 + 1.0 and 1.0 + 2.0 kg/ha mixture also controls Lol. mul., Sin. Arv., Stel. med., Alop. myos. and Matri. Cham., while providing near-adequate control for Av. fat.; and the 0.25 + 1.0 kg/ha also controls Lol. mul., Sin. Arv., Stel. med., and Matric cham.

Further, whereas it requires more than 1.0 kg/ha of methabenzthiazuron and more than 4.0 kg/ha of terbuchlor individually to control Stel. med., (with no selectivity to either wheat or barley as regards terbuchlor), this weed is selectively controlled in wheat and barley by a 0.25 + 0.5 or 0.5 + 0.5 kg/ha terbuchlor/methabenzthiazuron combination.

Further synergism of the combination herbicide of this invention is shown with respect to Sin. Arv., which, when treated with each chemical individually, requires substantially more than 4.0 kg/ha of terbuchlor and at least 1.0 kg/ha of methabenzthiazuron for control, with no safety whatever in wheat or barley as regards terbuchlor above 1.0 kg/ha. However, Sin. Arv. is selectively controlled with as little as 0.25 + 0.5 and 0.5 to 0.25 kg/ha terbuchlor/methabenzthiazuron mixtures. Sin. Arv. is also controlled with 0.5 + 0.5 kg/ha and other low ratio mixtures of these chemicals.

Similarly, about 3.0 and 4.0 kg/ha of terbuchlor and methabenzthiazuron, respectively are required to control Av. fat. when separately applied but with no safety to wheat or barley. However, this weed is effectively controlled with safety in wheat and barley with 1.0 + 1.0, 1.0 + 2.0 and 2.0 + 1.0 kg/ha terbuchlor/methabenzthiazuron mixtures. A 0.5 + 2.0 kg/ha mixture is safe for use in wheat, but control of Av. fat. is reduced somewhat, i.e. to 80%.

A Tammes isobole graphic representation of the synergistic effect of terbuchlor/methabenzthiazuron combinations would show on a coordinate graph the concentration in kg/ha required to achieve $GR_{85}$, for example, with methabenzthiazuron rates shown along the ordinate (horizontal axis) and terbuchlor rates shown along the abscissa (vertical axis). A line is then drawn to join the $GR_{85}$ rates for each compound; this line is the additive isobole for the mixture. Then holding one of the component rates constant while varying the rate of the other component, data points for each $GR_{85}$ rate are fixed on the graph. Any combination of weight ratios falling inside (or under) the additive isobole and having a $GR_{85}$ rate for weeds should exhibit synergism, and the corresponding interpolated curve is termed the synergistic isobole. Combinations having $GR_{85}$ data points falling outside (or above) the additive isobole should exhibit antagonism and the corresponding interpolated curve is termed the antagonistic isobole. Data points falling on the additive isobole line itself represent mixtures whose combined components have only additive effects. If a particular herbicidal combination has a $GR_{85}$ rate for weeds within the area under the additive isobole for that combination, but the data also exhibits injury to the crop greater than 15% at that rate, obviously, the herbicidal combination may not be selective for use in that particular crop under the specific test conditions.

In specific applications of the Tammes isoboles method, data derived from Table 1 is tabulated in Tables 2 and 3 showing the application rates (in kg/ha) for the individual components terbuchlor and methabenzthiazuron and various concentration ratios of each in mixtures thereof required to achieve $GR_{85}$ for the specific weeds, *Avena fatua* and *Sinapis arvensis*, respectively. Data points for the $GR_{85}$ rates are fixed on the graph below the additive isobole and a line of best fit is drawn through the data points to derive a curve termed the "interpolative synergistic isobole". The $GR_{85}$ data point for *Sin. arv.* with terbuchlor has not been experimentally determined, but is well over 4.0 kg/ha; by extrapolation it has been determined that about 8.5 kg/ha of terbuchlor is required.

Table 2

*Avena fatua*
$GR_{85}$ Rates (Kg/Ha)

| Terbuchlor |
|---|
| 3.0 |

| Methabenzthiazuron |
|---|
| 4.0 |

| Terbuchlor | + | Methabenzthiazuron |
|---|---|---|
| 0.5 | | >2.0 (ca 2.1) |
| 1.0 | | >1.0 (ca 1.1) |
| 2.0 | | 0.5 |

Table 2-continued

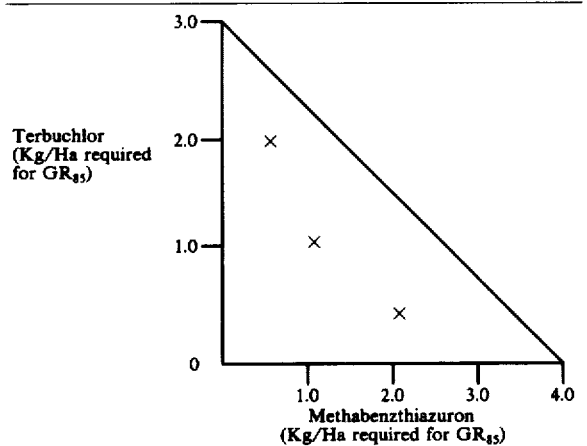

Table 3

*Sinapis arvensis*
GR₈₅ rates (kg/ha)

| Terbuchlor |
|---|
| 8.5 |

| Methabenzthiazuron |
|---|
| 1.1 |

| Terbuchlor | + | Methabenzthiazuron |
|---|---|---|
| 0.125 | | 1.0 |
| 0.250 | | <0.5 |
| 0.50 | | 0.25 |

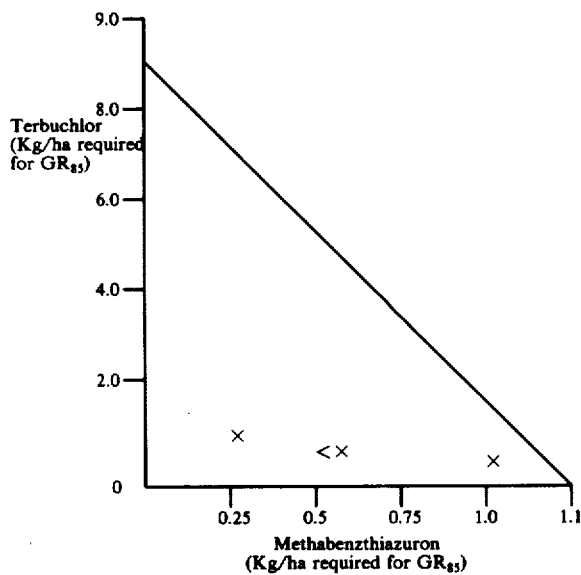

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surfce-active agents which can be used in herbicidal formulations are well known to those skilled in the art and have been well documented in patents, bulletins and textbooks.

The preparation, formulations and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plant, etc. In general, however, amounts ranging from about 0.05 to 6.0 or more kg/ha should be adequate; a preferred range being from about 0.125 to 4.0 kg/ha or suitably, an amount within the range of from 0.250 to 2.0 kg/ha. Terbuchlor/methabenzthiazuron ratios may vary within fairly wide limits, e.g., from 1:8 to 8:1, a preferred ratio being within the range of from 1:4 to 4:1 or even 1:2 to 2:1.

Modes of application of the herbicidal compositions of this invention to the plant are well-known to those skilled in the art. The application of liquid and particulate solid herbicidal formulations to the above-ground portions of plants can be carried out by conventional methods, e.g., power dusters, boom and hand sprayers and spray dusters. Although in more practical and recommended usage, the herbicidal compositions herein should be applied simultaneously as conjugate components in a mixture. However, it is within the purview of this invention to apply the individual components sequentially in either order, the time interval between successive applications being such as to accomplish the object of this invention, i.e., the supplementary/complementary/synergistic effects of terbuchlor/methabenzthiazuron combination.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. A herbicidal composition consisting essentially of a a herbicidally effective amount of a mixture of (a) N-(butoxymethyl)-6'-tert-butyl-2-chloro-o-acetotoluidide and (b) N-(2-benzthiazolyl-N,N'-dimethylurea wherein the ratio of (a) to (b) is within the range of from about 1:8 to 4:1 and an inert carrier therefor.

2. Composition according to claim 1 wherein components (a) and (b) together comprise from about 0.5% to 95% by weight of said composition, the balance comprising adjuvant.

3. Composition according to claim 2 wherein the ratio of (a) to (b) is within the range of from about 1:4 to 4:1.

4. A method for controlling undesirable plants associated with cereal crops which comprise applying to the locus of said plants a herbicidally effective amount of a mixture of (a) N-(butoxymethyl)-6'-tert-butyl-2-chloro-o-acetotoluidide and (b) N-(2-benzthiazolyl)-N,N'-dimethylurea wherein the ratio of (a) to (b) is within the range of from about 1:8 to 4:1.

5. Method according to claim 4 wherein said mixture is applied at a rate within the range of from about 0.375 to 3.0 Kg./ha.

6. Method according to claim 5 wherein the ratio of (a) to (b) is within the range of from about 1:4 to 4:1.

7. Method according to claim 5 wherein said mixture is applied at a rate within the range of from about 0.125 to 4.0 kg/ha.

8. Method according to claim 4 wherein said crops are wheat and barley.

* * * * *